United States Patent [19]
Yamane

[11] Patent Number: 6,033,851
[45] Date of Patent: Mar. 7, 2000

[54] METHOD FOR SUPPRESSING NONSPECIFIC HYBRIDIZATION IN PRIMER EXTENSION METHOD

[75] Inventor: Akio Yamane, Takata-gun, Japan

[73] Assignee: Wakunaga Seiyaku Kabushiki Kaisha, Osaka, Japan

[21] Appl. No.: 08/849,075

[22] PCT Filed: Dec. 11, 1995

[86] PCT No.: PCT/JP95/02535

§ 371 Date: May 30, 1997

§ 102(e) Date: May 30, 1997

[87] PCT Pub. No.: WO96/17932

PCT Pub. Date: Jun. 13, 1996

[30] Foreign Application Priority Data

Dec. 9, 1994 [JP] Japan ..................................... 6-306441

[51] Int. Cl.[7] .............................. C12Q 1/68; C07H 21/02; C07H 21/04; C12P 19/34
[52] U.S. Cl. ............................ 435/6; 536/23.1; 536/24.3; 435/91.2
[58] Field of Search .................................. 435/91.2, 5, 6; 935/77, 78; 536/23.1, 24.3

[56] References Cited

U.S. PATENT DOCUMENTS

| | | |
|---|---|---|
| 4,675,283 | 6/1987 | Roninson . |
| 4,683,202 | 7/1987 | Mullis et al. .............................. 435/91 |
| 4,965,188 | 10/1990 | Mullis et al. ............................... 435/6 |
| 5,043,272 | 8/1991 | Hartley ....................................... 435/91 |
| 5,348,853 | 9/1994 | Wang et al. ................................. 435/6 |
| 5,409,818 | 4/1995 | Davey et al. ......................... 435/91.21 |
| 5,411,875 | 5/1995 | Jones . |
| 5,556,752 | 9/1996 | Lockhart et al. . |
| 5,565,340 | 10/1996 | Chenchik et al. . |
| 5,605,793 | 2/1997 | Stemmer ..................................... 435/6 |
| 5,674,683 | 10/1997 | Kool . |
| 5,681,702 | 10/1997 | Collins et al. . |

OTHER PUBLICATIONS

Evander et al., J. of Virological Methods 31 : 239–250 (1991).

Chou et al., Nucleic Acids Research 20(7) : 1717–1723 (1992).

*Primary Examiner*—W. Gary Jones
*Assistant Examiner*—Ethan Whisenant
*Attorney, Agent, or Firm*—Oblon, Spivak, McClelland, Maier & Neustadt, P.C.

[57] ABSTRACT

An object of the present invention is to suppress nonspecific extension reaction of the primer in the primer extension method.

The primer extension reaction to form a nucleic acid strand complementary to a nucleic acid template strand with the use of a primer according to the present invention is characterized in that the reaction between the primer and the template strand is carried out in the presence of a nucleic acid or a derivative thereof which is complementary to said primer and has an affinity for said primer is equivalent to or less than that of said primer for the nucleic acid template strand.

28 Claims, No Drawings

METHOD FOR SUPPRESSING NONSPECIFIC HYBRIDIZATION IN PRIMER EXTENSION METHOD

BACKGROUND OF THE INVENTION

1. Field of Invention

The present invention relates to a method for suppressing nonspecific extension of primers in the primer extension method.

2. Background Art

The primer extension reaction, which forms a nucleic acid complementary to a nucleic acid template, not only has an important role in an organism but is also used as an essential technique in genetic engineering. In the reaction, a template and a primer which is complementary to the template form a double strand, and then polymerase adds the mononucleotides complementary to the template at the 3' end of the primer. Vary et al. proposed a method of detecting nucleic acids using the above template-dependent primer extension reaction (U.S. Pat. No. 4,851,331).

Various gene amplification methods utilizing the above primer extension method (for example, the PCR method, SDA method, RCR method, NASB method, 3SR method: Keller, G. H. et al., DNA Probes, pp. 255–297, Stockton Press (1993); Persing, D. H. et al., Diagnostic Molecular Microbiology, pp. 51–87, American Society for Microbiology (1993)) have been developed, which have significantly contributed to the advancement of genetic engineering.

However, in these gene amplification methods using the primer extension method, excessive amounts of reagents (polymerase, primer, unit nucleic acid, etc.) relative to a template gene to be amplified are necessary in the early stages of the reaction in order to amplify the gene by about million times. Therefore, nonspecific hybridizations are very likely to occur (Chou et al., Nucleic Acids Res., 20, 1717 (1992)). Furthermore, even in the PCR method which is believed to be the best in terms of specificity, it is difficult to perform highly specific amplification when the amount of template nucleic acid is extremely small, or the presence of large quantities of impurities derived from a sample. Also, primer dimers were found to cause an unexpected problem in the PCR method (Li et al., Proc. Natl. Acad. Sci. USA. 87, 4580–4584 (1990)).

To solve the above problems, the Hot Start Method (Chou et al., Nucleic Acids Res. 20, 1717–1723 (1992)), a method using a polymerase antibody (Kellogg et al., Bio Techniques 16, 1134–1137 (1994); Sharkey et al., BIO/TECHNOLOGY 12, 506–507 (1994)), and others have been proposed. However, none of these methods can sufficiently suppress nonspecific hybridization nor nonspecific extension reaction after the start of the PCR reaction, and cannot be applied to any other amplification method except the PCR method. A nested PCR method using 2 sets of primers (Pierre et al., J. Clin. Microbiol. 29, 712–717 (1991)) definitely improves specificity; however, this method is considered to be procedurally unpractical.

SUMMARY OF THE INVENTION

An object of the present invention is to provide a method for suppressing nonspecific hybridization in the primer extension method.

Another object of the present invention is to provide a reagent to suppress nonspecific hybridization of a primer to a nucleic acid template strand in the primer extension method.

According to the present invention, there is provided a primer extension reaction method to form a nucleic acid strand complementary to a nucleic acid template strand by a primer, characterized in that the reaction between the primer and the template strand is carried out in the presence of a nucleic acid or a derivative thereof which is complementary to said primer and has an affinity for said primer which is equivalent to or less than that of said primer for the nucleic acid template strand (primer-complementary nucleic acid).

According to the present application, there is also provided a reagent to suppress nonspecific hybridization of a primer with a nucleic acid template strand comprising a nucleic acid or a derivative thereof which is complementary to said primer and has an affinity for said primer which is equivalent to or less than that of said primer for the nucleic acid template strand.

According to the present invention, nonspecific hybridization in the primer extension reaction is suppressed. This is considered to be due to the decrease in nonspecific hybridization of the primer to the nucleic acid template strand in the presence of the nucleic acid complementary to the primer.

DETAILED DESCRIPTION OF THE INVENTION

The term "nucleic acid" herein refers to nucleic acids comprising ribonucleotides and/or deoxyribonucleotides, which include DNA, RNA and oligonucleotides comprising a mixture of ribonucleotides and deoxyribonucleotides.

Furthermore, the term "nucleic acid derivative" herein refers to derivatives in which atoms (e.g., a hydrogen atom, oxygen atom) or functional groups (e.g., a hydroxyl group, amino group) of the base, ribose, phosphoric acid diester bond, or other moieties of a nucleic acid are substituted by other atoms (e.g., a hydrogen atom, sulfur atom), functional groups (e.g., an amino group), or alkyl groups having 1–6 carbon atoms; or are protected by protecting groups (e.g., a methyl group or acyl group); or said portions are substituted by non-natural type moieties (e.g., peptides).

Examples of such derivatives include a peptide nucleic acid (PNA) in which base moieties are bonded by peptide bonds (Nielsen et al., J. Amer. Chem. Soc., 114, 9677–9678 (1992)), rare nucleic acids found in nature (Nucleic Acids Research, 22 (2), 2183 (1994)), nucleic acids in which hydrogen atoms of amino groups of base moieties are substituted by alkyl groups having 1–6 carbon atoms, nucleic acids in which the stereo configuration of the hydroxyl groups of ribose moieties is changed, and nucleic acids in which oxygen atoms of phosphoric acid diester bond portions are substituted by sulfur atoms.

Furthermore, the term "primer" refers to nucleic acid molecules and their derivatives which are required at the start of the reaction for nucleic acid synthesis. Accordingly, the above DNA and RNA and their derivatives may also be used as the primers.

The method according to the present invention is primarily the primer extension reaction which forms a nucleic acid chain complementary to a nucleic acid template strand by a primer, wherein the reaction between the primer and the template strand is carried out in the presence of a nucleic acid or a derivative thereof which is complementary to said primer and has an affinity for said primer which is equivalent to or less than that of said primer for the nucleic acid template strand (primer-complementary nucleic acid). As used hereinafter, the term "primer-complementary nucleic acid" includes their derivatives.

One theory for the suppression of the nonspecific hybridization is as follows, but not limited to. First, nonspecific hybridization is a phenomenon in which the primer is hybridized at a site other than the target region where the primer is supposed to be hybridized and thus a sequence other than the target sequence is formed starting from this site. If a primer-complementary nucleic acid which is complementary to the primer and has the affinity for said primer which is equivalent to or less than that of the primer for the template strand is present here, this primer-complementary nucleic acid could be attracted to and hybridize with that portion of the primer which is not hybridized to the target site. As a result, the primer is less likely to hybridize to a site other than the target region, thereby suppressing nonspecific hybridization. Further, since the affinity of the primer-complementary nucleic acid for the primer is equal to or less than that of the template strand for the primer, the primer-complementary nucleic acid has no adverse effect on the hybridization of the primer to the target region.

The term "affinity" herein can be used, for example, by heat stability of a compound as expressed by its melting temperature (Tm) (Higgins et al., Nucleic Acid Hybridization, p. 80, IRL PRESS (1985)). Namely, a large Tm value means high affinity and a small Tm value means low affinity.

One method to reduce the affinity between the primer-complementary nucleic acid and the primer is to make the primer-complementary nucleic acid chain shorter than the primer. Since nonspecific hybridization becomes more of an important factor at site closer to the 3' end of the primer, it is desirable to shorten the primer-complementary nucleic acid from the 3' end. The chain length of the primer-complementary nucleic acid can be appropriately determined by taking the affinity into consideration. For example, it is preferably 1–0.4, more preferably 0.9–0.6, when the chain length of the primer is set to be 1.

Furthermore, the affinity can be reduced by introducing a nucleotide which is not complementary to the primer into the primer-complementary nucleic acid. The affinity can also be reduced by introducing a base which is complementary to that of the primer but forms a complementary strand with a weaker hydrogen bond, for example, inosine (Martin et al., Nucleic Acids Res. 13, 8927–8938 (1985)).

It is preferable to previously inactivate the primer extension activity of the primer-complementary nucleic acid as used in the present invention since the primer-complementary nucleic acid itself can function as a primer. The inactivation can be done, for example, by deoxygenation of the 3' end (for example, deoxygenation of the 3'-end nucleotide to 2', 3'-dideoxyribonucleotide) or by protection with a protecting group (for example, a methyl group or acyl group).

In a preferred embodiment of the present invention, the primer and the primer-complementary nucleic acid bond together to form one molecule. If the primer-complementary nucleic acid is in very close proximity to the primer, that is, both strands are in the same molecule, the primer portion can be easily caught by the primer-complementary nucleic acid to form an intramolecular bond when the primer is not hybridized to the target template strand. In this way, nonspecific hybrid formation can be effectively suppressed.

Accordingly, the term "one molecule" refers to a condition in which the primer-complementary nucleic acid is directly or indirectly bound to the primer through a mode other than hybridization (for example, covalent bond).

The method used to form the one molecule should preferably not reduce hybridization ability of the primer to the primer-complementary nucleic acid. Examples of bonding sites which do not reduce the hybridization are the hydroxyl group, the base moiety, and the phosphoric acid diester at the 5' end for the primer, and the hydroxyl group, the base moiety, and the phosphoric acid diester portion at the 5' end or 3' end for the primer-complementary nucleic acid.

More specifically, for example, the one molecule is formed by a method in which an oligonucleotide is modified (Ecrstein, Oligonucleotides and Analogues, IRL PRESS (1991)) to incorporate a linker and the two are cross-linked using a commercially available cross-linking agent.

Any length of the linker may be appropriate as long as it does not reduce hybridization between the primer and the primer-complementary nucleic acid. The appropriate length depends on the length of the primer and the primer-complementary nucleic acid or the site of cross-linking; for example, a distance of 3–50 atoms (preferably 5–30 atoms) is appropriate. The linker may consist of any elements as long as they do not affect hybridization of the primer to the primer-complementary nucleic acid, or the primer extension reaction.

Examples of the linker include saturated or unsaturated hydrocarbon groups, alicyclic hydrocarbon groups, aromatic hydrocarbon groups and heterocyclic groups. Examples of the saturated hydrocarbons include alkyl groups having 3–50 carbons, preferably alkyl groups having 5–30 carbons, more preferably alkyl groups having 5–10 carbons.

The linker molecule may contain ester bonds, ether bonds, peptide bonds, oxygen atoms, sulfur atoms and nitrogen atoms alone or in combination, and one or more of its hydrogen atoms may be substituted by a carboxyl group, amino group, alkoxy group, acyl group, alkoxycarbonyl group, acyloxy group, hydroxyl group or a halogen atom. The linker can be a normal chain or can contain branched chains. The linker is preferably hydrophilic and it may contain, for example, ether bonds, peptide bonds or the like.

The cross-linking is carried out, for example, by a method in which linkers having an amino group and thiol group are introduced into both nucleic acids and, after that, the nucleic acids are cross-linked using a bifunctional cross-linking agent (for example, N-(6-maleimido-caproyloxy) succinimide (EMCS), N-succinimidyl-3-(2-pyridyldithio) propionate (SPDP)). The cross-linking can also carried out by using a reagent to introduce a spacer between nucleotides (Nelson et al., Nucleic Acids Res. 20, 6253–6259 (1992)) and synthesizing the primer and the primer-complementary nucleic acid in sequence using a DNA synthesizer.

The term "primer extension reaction" herein refers to a reaction in which a nucleic acid complementary to a nucleic acid template strand is added to the 3' end of a primer using polymerase. Examples of processes in which the primer extension method is used include gene amplification methods, such as the Polymerase Chain Reaction (PCR method), Self-sustained Sequence Replication method (3SR method), Nucleic Acid Based Amplification method (NASBA method), Repair Chain Reaction method (RCR method), Strand Displacement Amplification method (SDA method), Polymerase/Ligase Chain Reaction method (P/LCR method), and the Sanger method.

The primer extension reaction can be carried out in a reaction solution containing a nucleic acid template strand, a primer, polymerase, mononucleotides, etc. First, the reaction solution is placed under hybridization conditions (for example at a temperature lower than the melting temperature) and then the primer is extended using polymerase.

The amount of the primer-complementary nucleic acid in the reaction solution can be appropriately determined by taking into consideration the suppression of specific and nonspecific binding of the primer to the template strand. For example, the amount is preferably more than one mole, more preferably 2–10 moles, per one mole of primer.

Furthermore, the reaction solution can contain a nucleic acid template strand, polymerase, mononucleotides, etc. The nucleic acid template strand can be DNA or RNA, or a derivative thereof. Examples of polymerase to be used include, but are not restricted to, DNA polymerase, RNA-dependent DNA polymerase (reverse transcriptase) and RNA polymerase. Examples of mononucleotides include ribonucleotides and deoxyribonucleotides and derivatives thereof (for example, a derivative in which the 3' hydroxyl group is deoxygenated) or mixtures thereof.

In order to suppress nonspecific hybridization, the primer-complementary nucleic acid can be included in the reaction solution, or added to the reaction solution just before the primer extension reaction starts.

Another embodiment of the present invention provides a reagent to suppress nonspecific hybridization of a specified primer to a nucleic acid template strand in the primer extension method, comprising a nucleic acid which is complementary to said primer and has an affinity for said primer which is equivalent to or less than that of said primer for the nucleic acid template strand, or a derivative thereof.

The term "specified primer" refers to a primer which is specified in relation to the template nucleic acid in the reagent, and the nucleic acid complementary to this primer is specified accordingly. For example, when the template nucleic acid is the protein A gene of *Staphylococcus aureus*, the specified primer is a nucleic acid having a sequence complementary to the target gene, for example, SPA1 and SPA2 as described in Example 1.

The amount of the above nucleic acid complementary to the primer in the nonspecific hybridization suppressing reagent and the allowable constituents in the reagent can be the same as mentioned above.

EXAMPLE

The present invention will be explained by the following examples; however, the invention is not intended to be limited to these examples.

Oligodeoxyribonucleotide synthesis in the present invention was carried out according to the phosphoramidite method (Caruthers et al., Tetrahedron Lett., 22, 1859 (1981)) using a DNA synthesizer, Model 381 A (Applied Biosystems). An oligonucleotide labeled at the 5' end was prepared by firstly introducing 5' end amino group into an oligonucleotide and then labeling with an appropriate labeling reagent (for example, biotin group, dinitrophenol group (DNP)). Further, an oligonucleotide with an amino group introduced in the 3' end was prepared according to the method by Nelson et al. (Nelson et al., Nucleic Acids Res., 17, 7187–7194 (1989)). The PCR reaction was carried out according to the method described in PCR Protocols (Innis, M. A. S. Academic Press (1990)).

Amplification by the PCR reaction was carried out according to the ED-PCR method (Japanese Patent Laid-open No. 252300/1989).

Example 1

Detection of Specified Gene by PCR Method

Protein A gene unique to *Staphylococcus aureus* was used as the specified gene (Shuttleworth H. L. et al., Gene 58, 283–295 (1987)). A part of the gene coding for Protein A (224 base pairs) was specifically amplified according to the PCR method using the following set of primers, and confirmed by agarose gel electrophoresis.

SPA1: 5'-BIO-TACATGTCGTTAAACCTGGTG-3'(SEQ ID NO:1)

SPA2: 5'-DNP-TACAGTTGTACCGATGAATGG-3' (SEQ ID NO:2)

A biotin (BIO) group and a dinitrophenol (DNP) group were introduced at the 5' ends of SPA1 and SPA2, respectively.

PCR products produced by the ED-PCR method using the above primers were detected as follows.

First, a PCR reaction solution of the following composition was prepared.

| | |
|---|---|
| 10 × Amplitaq (trade name) reaction solution | 5 μl |
| 20 mM dNTP | 0.5 μl |
| SPA1 50 ng/μl | 1 μl |
| SPA2 50 ng/μl | 1 μl |
| Amplitaq (trade name) DNA polymerase (1.25U/μl) | 1 μl |
| H$_2$O | 41.5 μl |

The PCR reaction was carried out using the above reaction solution with and without *Staphylococcus aureus* DNA (400 pg/μl, 1 μl) as a template DNA. SPA1 and SPA 2 were used as primers. The PCR reaction was carried out for 35 cycles, where one cycle was 30 seconds at 94° C., 30 seconds at 50° C. and 60 seconds at 72° C. The reaction was performed in the reaction solution (10 μl) supplemented with an alkaline phosphatase-labeled antibody on a streptoavidin plate. After 30 minutes, the reaction solution was removed and the plate was washed 3 times with a washing solution. Finally, a buffer solution and a coloring substrate (1 M diethanolamine amine (pH 9.8), 0.5 mM MgCl$_2$, 4 mg/ml p-nitrophenylphosphoric acid phosphate) were added to the plate for a color reaction, and optical density was measured using a plate reader.

Color development, expressed by the optical density after 10 minutes, with and without *Staphylococcus aureus* DNA (400 pg) was 1.80 and 0.01, respectively. When the PCR reaction was carried out for 40 cycles, color development after 10 minutes with and without *Staphylococcus aureus* DNA (400 pg) was 1.93 and 1.00, respectively.

In other words, the detection of positive and negative reactions for *Staphylococcus aureus* became difficult when the number of cycles of the PCR reaction was increased from 35 to 40.

Example 2

Suppression of Nonspecific Extension Reaction in PCR Method (1)

Oligonucleotides complementary to primers SPA1 and SPA2 were synthesized and tested for their suppression of the nonspecific extension reaction in the PCR method.

SPA1-C1: 5'-CACCAGGTTTAAC-3' NH$_2$ (SEQ ID NO:3)

SPA2-C1: 5'-CCATTCATCGGTA-3' NH$_2$ (SEQ ID NO:4)

SPA1-C1 has a sequence complementary to the 13 bases from the 3' end of the primer SPA1 and SPA2-C1 has a sequence complementary to the 13 bases from the 3' end of the primer SPA2. Furthermore, an amino group (NH$_2$) was incorporated at the 3' end of the oligonucleotides complementary to each primer.

PCR reaction solutions having the compositions below were prepared and the PCR reaction was carried out using SPA1 and SPA2 as primers. The PCR reaction was carried out for 40 cycles, where one cycle was 30 seconds at 94° C., 30 seconds at 50° C. and 60 seconds at 72° C.

| Reaction solution 1 | |
| --- | --- |
| 10 × Amplitaq (trade name) reaction solution | 5 µl |
| 20 mM dNTP | 0.5 µl |
| SPA1 50 ng/µl | 1 µl |
| SPA2 50 ng/µl | 1 µl |
| Amplitaq (trade name) DNA polymerase (1.25 U/µl) | 1 µl |
| SPA1-C1 500 ng/µl | 5 µl |
| SPA2-C1 500 ng/µl | 5 µl |
| $H_2O$ | 31.5 µl |
| Reaction solution 2 | |
| 10 × Amplitaq (trade name) reaction solution | 5 µl |
| 20 mM dNTP | 0.5 µl |
| SPA1 50 ng/µl | 1 µl |
| SPA2 50 ng/µl | 1 µl |
| Amplitaq (trade name) DNA polymerase (1.25 U/µl) | 1 µl |
| SPA1-C1 500 ng/µl | 10 µl |
| SPA2-C1 500 ng/µl | 10 µl |
| $H_2O$ | 21.5 µl |
| Reaction solution 3 | |
| 10 × Amplitaq (trade name) reaction solution | 5 µl |
| 20 mM dNTP | 0.5 µl |
| SPA1 50 ng/µl | 1 µl |
| SPA2 50 ng/µl | 1 µl |
| Amplitaq (trade name) DNA polymerase (1.25 U/µl) | 1 µl |
| $H_2O$ | 41.5 µl |

The PCR reaction was carried out for each reaction solution with or without the addition of *Staphylococcus aureus* DNA (400 pg/µl, 1 µl), and optical density was measured in the same manner as described in Example 1.

Color development after 12 minutes was as follows:

| | Reaction solution | | |
| --- | --- | --- | --- |
| | 1 | 2 | 3 |
| Without template | 0.05 | 0.04 | 1.57 |
| With *S. aureus* DNA template | 2.12 | 1.22 | 2.47 |

Example 3

Suppression of Nonspecific Extension Reaction in PCR Method (2)

Suppression of nonspecific extension reaction in the PCR method was attempted using the following oligonucleotides SPA1-C2 and SPA2-C2 complementary to primers SPA1 and SPA 2, respectively

SPA1-C2: 5'-CACCAGGTTTAACGACAT-3' $NH_2$ (SEQ ID NO:5)

SPA2-C2 :5'-CCATTCATCGGTACAACT-3' $NH_2$ (SEQ ID NO:6)

SPA1-C2 was complementary to 18 bases from the 3' end of the primer SPA1 and SPA2-C2 was complementary to 18 bases from the 3' end of the primer SPA2.

PCR reaction solutions having the compositions below were prepared and the PCR reaction was carried out using SPA1 and SPA2 as primers. The PCR reaction was carried out for 40 cycles, where one cycle was 30 seconds at 94° C., 30 seconds at 50° C. and 60 seconds at 72° C.

| Reaction solution 4 | |
| --- | --- |
| 10 × Amplitaq (trade name) reaction solution | 5 µl |
| 20 mM dNTP | 0.5 µl |
| SPA1 50 ng/µl | 1 µl |
| SPA2 50 ng/µl | 1 µl |
| Amplitaq (trade name) DNA polymerase (1.25 U/µl) | 1 µl |
| $H_2O$ | 41.5 µl |
| Reaction solution 5 | |
| 10 × Amplitaq (trade name) reaction solution | 5 µl |
| 20 mM dNTP | 0.5 µl |
| SPA1 50 ng/µl | 1 µl |
| SPA2 50 ng/µl | 1 µl |
| Amplitaq (trade name) DNA polymerase (1.25 U/µl) | 1 µl |
| SPA1-C2 500 ng/µl | 1 µl |
| SPA2-C2 500 ng/µl | 1 µl |
| $H_2O$ | 39.5 µl |

The PCR reaction was carried out for each reaction solution above and optical density was measured in the same manner as described in Example 2. Furthermore, a similar experiment was carried out with solutions supplemented with human DNA (700 ng per reaction) as a template.

Color development after 10 minutes was as follows:

| | Reaction solution | |
| --- | --- | --- |
| | 4 | 5 |
| Without template | 0.35 | 0.00 |
| With human DNA template (700 ng) | 0.09 | 0.00 |
| With *S. aureus* DNA template (400 ng) | 2.21 | 1.16 |

Example 4

Suppression of Nonspecific Extension Reaction in PCR Method (3)

(1) Synthesis of primer bound to primer-complementary nucleic acid

Primers bound to primer-complementary nucleic acids, as shown below, were synthesized.

SPA1C: 5' BIO-CACCAGGTTTAAC(SEQ ID NO:3)-(linker)-TACATGTCGTTAAACCTGGTG(SEQ ID NO:1)

SPA2C: 5'DNP-CCATTCATCGGTA(SEQ ID NO:4)-(linker)-TACAGTTGTACCGATGAATGG(SEQ ID NO:2)

For SPA1C, the primer part was synthesized first, according to the general oligonucleotide synthesis method. The sequence above was sequentially added from the 3' end, and after the base of the 5' end of the primer was added, C6-Thiol Modifier (trade name, Clonetech) was added to introduce a thiol group. The product so synthesized was removed from the carrier and the protecting groups were removed according to conventional methods. A crude product was obtained by gel filtration (Sephadex G-50, 50 mM TEAB buffer, pH 7.2). The crude product (10 $A_{260}$ units) was dried by evaporation and dissolved in 100 µl of 0.1 M TEAA (triethylammonium acetate) of pH 7.5. 1 M $AgNO_3$ (15 µl) was added and the mixture was allowed to react at room temperature for 30 minutes. Next, 10 µl of 1.0 M DTT (dithiothreitol) was added, and the reaction was continued at room temperature for 15 minutes. The precipitate so formed was removed by centrifugation and purified by gel filtration (Sephadex G-50, 40 mM phosphate buffer, pH 6.0). The resulting eluate was used for the next reaction.

The portion complementary to the primer was synthesized as follows. In order to introduce an amino group at the 3' end, using the carrier of the Nelson method (Nelson, Nucleic acids Res., 17, 7187–7194 (1989)), the base sequence complementary to the primer was sequentially added. After the addition of the last base, Biotin ON Phosphoramidite (Clonetech) was added to the 5' end to introduce the biotin moiety. The product so synthesized was removed from the carrier and the protecting groups were removed according to conventional methods. A crude product was obtained by gel filtration (Sephadex G-50, 50 mM TEAB buffer, pH 7.2). The crude product (10 $A_{260}$ units) was dried by evaporation and dissolved in 40 µl of water. 1 M $NaHCO_3$ (10 µl) was added, then 50 µl of a DMF solution of EMCS (Dojindo, 20 mg/ml) was added, and the reaction was carried out at room temperature for 5 hours. After the reaction, the reagent was removed by gel filtration (Sephadex G-50, 50 mM TEAB buffer, pH 7.2).

The above two kinds of oligonucleotides were bound to each other as follows. First, the oligonucleotide having biotin at the 5' end and the amino group at the 3' end was dried by evaporation, to which the entire volume of the phosphate buffer solution of the oligonucleotide with the thiol group at the 5' end was added. The admixture was allowed to react at room temperature for 16 hours. After the reaction, the buffer was exchanged by gel filtration (Sephadex G-50, 50 mM TEAB buffer, pH 7.2), and the resultant solution was dried by evaporation. The resultant mixture was purified by gel electrophoresis with 20% polyacrylamide containing 8.3 M urea. The oligonucleotide was recovered from the band of slower mobility to obtain SPA1C primer bound to the primer-complementary nucleic acid.

SPA2C primer was synthesized in the same manner except that DNP-ON Phosphoramidite (Clonetech) was used to introduce DNP at the 5' end in synthesizing the part complementary to the primer.

(2) Suppression of nonspecific aplification reaction by primers SPA1C and SPA2C

A reaction solution having the composition below was prepared, and the primer bound to the nucleic acid complementary to the primer was tested for its effect in suppressing the nonspecific extension reaction.

| 10 × Amplitaq (trade name) reaction solution | 5 µl |
| 20 mM dNTP | 0.5 µl |
| SPA1C 100 ng/µl | 1 µl |
| SPA2C 100 ng/µl | 1 µl |
| Amplitaq (trade name) DNA polymerase (1.25 U/µl) | 1 µl |
| $H_2O$ | 41.5 µl |

The PCR reaction was carried out for each reaction solution without template or with Staphylococcus aureus DNA template or human DNA template. Optical density was measured in the same manner as described in Example 1. Color development after 10 minutes was as follows:

| | |
|---|---|
| Without template | 0.00 |
| With human DNA template (700 ng) | 0.00 |
| With S. aureus DNA templage (400 ng) | 0.53 |

As shown above, nonspecific amplification reaction was suppressed; however, specific amplification was also suppressed.

(3) Results with primers bound to shortened primer-complementary nucleic acid

Primers bound to shortened primer-complementary nucleic acids as shown below were synthesized in the same manner as described in (1), and studied.

SPA1CS: 5' BIO-CACCAGGT(SEQ ID NO:7)-(linker)-TACATGTCGTTAAACCTGGTG(SEQ ID NO:1)

SPA2CS: 5' DNP-CCATTCAT(SEQ ID NO:8)-(linker)-TACAGTTGTACCGATGAATGG(SEQ ID NO:2)

The PCR reaction was carried out and optical density was measured under the same conditions as described in (2).

| | |
|---|---|
| Without template | 0.00 |
| With human DNA template (700 ng) | 0.00 |
| With S. aureus DNA template (400 ng) | 2.15 |

As shown above, by shortening the chain length of the primer-complementary nucleic acids, the specific amplification reaction was efficiently carried out while the nonspecific amplification reaction was suppressed.

What is claimed is:

1. A method for extending a primer comprising the steps of:

(a) providing a primer, a template, and a third nucleic acid molecule, wherein the primer is capable of specifically hybridizing to the third nucleic acid molecule, wherein the affinity of the primer for the third nucleic acid molecule is less than or equal to the affinity of the primer for the template, wherein the third nucleic acid molecule contains an inosine residue; and (b) incubating the primer, the template, and the third nucleic acid molecule together under conditions sufficient to extend the primer, thereby extending the primer.

2. A method for extending a primer comprising the steps of:

(a) providing a primer, a template, and a third nucleic acid molecule, wherein the primer is capable of specifically hybridizing to the third nucleic acid molecule, wherein the affinity of the primer for the third nucleic acid molecule is less than or equal to the affinity of the primer for the template, wherein the third nucleic acid molecule is covalently bonded to the primer; and (b) incubating the primer, the template, and the third nucleic acid molecule together under conditions sufficient to extend the primer, thereby extending the primer.

3. The method of claim 2, wherein the primer, the template, and the third nucleic acid molecule are each DNA or RNA.

4. The method of claim 2, wherein the third nucleic acid molecule is shorter than the primer.

5. The method of claim 2, wherein the third nucleic acid molecule contains a nucleotide which is not complementary to the primer.

6. The method of claim 2, wherein the third nucleic acid molecule contains a nucleotide which is capable of forming a weak hydrogen bond with the primer.

7. The method of claim 2, wherein the third nucleic acid molecule contains an inosine residue.

8. The method of claim 2, wherein the third nucleic acid molecule and the primer are bound to each other by a linker.

9. The method of claim 2, wherein the linker is a saturated hydrocarbon group, an unsaturated hydrocarbon group, an alicyclic hydrocarbon group, an aromatic hydrocarbon group, or a heterocyclic group.

10. The method of claim 9, wherein the linker is a saturated hydrocarbon group.

11. The method of claim 10, wherein the linker is an alkyl group containing from 5 to 30 carbon atoms.

12. The method of claim 2, wherein the nucleotide residue at the 3' end of the third nucleic acid molecule does not contain a hydroxyl group directly bonded to the carbon atom at position 3 of the ribose moiety, wherein a pair of hydrogen atoms, a functional group, or a protecting group is bonded to the carbon atom at position 3 of the ribose moiety.

13. The method of claim 2, wherein the third nucleic acid molecule is peptide nucleic acid (PNA).

14. The method of claim 2, wherein the primer is extended by the polymerase chain reaction method, the 3SR method, the NASBA method, the RCR method, the SDA method, the P/LCA method, or the Sanger method.

15. A method for extending a primer comprising the steps of:

(a) providing a primer, a template, and a third nucleic acid molecule, wherein the primer is capable of specifically hybridizing to the third nucleic acid molecule, wherein the $T_m$ of the primer binding to the third nucleic acid molecule is lower than the $T_m$ of the primer binding to the template; and (b) incubating the primer, the template, and the third nucleic acid molecule together under conditions sufficient to extend the primer, thereby extending the primer.

16. The method of claim 15, wherein the third nucleic acid molecule contains an inosine residue.

17. The method of claim 15, wherein the third nucleic acid molecule is covalently bonded to the primer.

18. The method of claim 15, wherein the primer, the template, and the third nucleic acid molecule are each DNA or RNA.

19. The method of claim 15, wherein the third nucleic acid molecule is shorter than the primer.

20. The method of claim 15, wherein the third nucleic acid molecule contains a nucleotide which is not complementary to the primer.

21. The method of claim 15, wherein the third nucleic acid molecule contains a nucleotide which is capable of forming a weak hydrogen bond with the primer.

22. The method of claim 15, wherein the third nucleic acid molecule and the primer are bound to each other by a linker.

23. The method of claim 15, wherein the linker is a saturated hydrocarbon group, an unsaturated hydrocarbon group, an alicyclic hydrocarbon group, an aromatic hydrocarbon group, or a heterocyclic group.

24. The method of claim 15, wherein the linker is a saturated hydrocarbon group.

25. The method of claim 15, wherein the linker is an alkyl group containing from 5 to 30 carbon atoms.

26. The method of claim 15, wherein the nucleotide residue at the 3' end of the third nucleic acid molecule does not contain a hydroxyl group directly bonded to the carbon atom at position 3 of the ribose moiety, wherein a pair of hydrogen atoms, a functional group, or a protecting group is bonded to the carbon atom at position 3 of the ribose moiety.

27. The method of claim 15, wherein the third nucleic acid molecule is peptide nucleic acid (PNA).

28. The method of claim 15, wherein the primer is extended by the polymerase chain reaction method, the 3SR method, the NASBA method, the PCR method, the SDA method, the P/LCA method, or the Sanger method.

* * * * *

SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:

(A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:1:

TACATGTCGT TAAACCTGGT G                                              21

(2) INFORMATION FOR SEQ ID NO:2:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:2:

TACAGTTGTA CCGATGAATG G                                              21

(2) INFORMATION FOR SEQ ID NO:3:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (xi) SEQUENCE DESCRIPTION: SEQ ID NO:3:

CACCAGGTTT AAC                                                       13

(2) INFORMATION FOR SEQ ID NO:4:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (xi) SEQUENCE DESCRIPTION: SEQ ID NO:4:

CCATTCATCG GTA                                                       13

(2) INFORMATION FOR SEQ ID NO:5:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:5:

CACCAGGTTT AACGACAT                                                  18

(2) INFORMATION FOR SEQ ID NO:6:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:6:

CCATTCATCG GTACAACT                                                  18

(2) INFORMATION FOR SEQ ID NO:7:

(i) SEQUENCE CHARACTERISTICS:
        (A) LENGTH: 8 base pairs

-continued

```
       (B) TYPE: nucleic acid
       (C) STRANDEDNESS: single
       (D) TOPOLOGY: linear (xi) SEQUENCE DESCRIPTION: SEQ ID NO:7:

CACCAGGT                                                              8

(2) INFORMATION FOR SEQ ID NO:8:

(i) SEQUENCE CHARACTERISTICS:
       (A) LENGTH: 8 base pairs
       (B) TYPE: nucleic acid
       (C) STRANDEDNESS: single
       (D) TOPOLOGY: linear (xi) SEQUENCE DESCRIPTION: SEQ ID NO:8:

CCATTCAT                                                              8
```